United States Patent
Zeller

(10) Patent No.: US 11,547,368 B2
(45) Date of Patent: Jan. 10, 2023

(54) SYSTEM AND METHOD FOR DETERMINING AN IMAGING MODALITY AND THE PARAMETERS THEREFOR

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 504 days.

(21) Appl. No.: 16/413,886

(22) Filed: May 16, 2019

(65) Prior Publication Data

US 2019/0350534 A1 Nov. 21, 2019

(30) Foreign Application Priority Data

May 16, 2018 (DE) ..................... 10 2018 207 632.4

(51) Int. Cl.
*A61B 5/00* (2006.01)
*A61B 5/113* (2006.01)
(Continued)

(52) U.S. Cl.
CPC ............ *A61B 5/7292* (2013.01); *A61B 5/024* (2013.01); *A61B 5/113* (2013.01); *A61B 5/318* (2021.01);
(Continued)

(58) Field of Classification Search
CPC ....... A61B 5/7292; A61B 5/318; A61B 5/024; A61B 5/113; A61B 5/7207; A61B 5/7264;
(Continued)

(56) References Cited

U.S. PATENT DOCUMENTS

| 2005/0251013 A1* | 11/2005 | Krishnan | G06T 7/0012 600/407 |
| 2005/0267348 A1* | 12/2005 | Wollenweber | A61B 6/544 600/407 |
| 2006/0239544 A1* | 10/2006 | Yankelevitz | G16H 50/30 382/156 |
| 2008/0219530 A1* | 9/2008 | Levanon | A61B 5/02007 702/19 |

(Continued)

FOREIGN PATENT DOCUMENTS

| EP | 3553548 A1 | 10/2019 |
| WO | 2018085788 A1 | 5/2018 |

OTHER PUBLICATIONS

Küstner, Thomas et al.: "Automated reference-free detection of motion artifacts in magnetic resonance images" In: Magnetic Resonance Materials in Physics, Biology and Medicine; 2017; doi:10.1007/s10334-017-0650-z.
(Continued)

*Primary Examiner* — Amelie R Davis
*Assistant Examiner* — Helene Bor
(74) *Attorney, Agent, or Firm* — Banner & Witcoff Ltd.

(57) ABSTRACT

In a method and system, a medical imaging modality and the parameters to be deployed for the determined imaging modality are determined to produce an image of an examination object using the determined imaging modality and the determined parameters. Information from the preliminary examination(s) of the examination object can be automatically classified to generate classification results corresponding to interfering influence(s) resulting from the production of the image. The classification results can be analyzed to evaluate the classification results. The medical imaging modality and the parameter(s) is determined, based on the evaluated results, to minimize an influence of the interfering influences of the classification results in image(s) of the examination object generated using the determined medical imaging modality and the determined one or more parameters. The image(s) may then be generated using the deter- (Continued)

mined medical imaging modality and the determined parameter(s).

20 Claims, 2 Drawing Sheets

(51) Int. Cl.
 *A61B 5/024* (2006.01)
 *A61B 5/318* (2021.01)
 *A61B 8/13* (2006.01)
 *A61B 5/055* (2006.01)
 *A61B 6/03* (2006.01)

(52) U.S. Cl.
 CPC .......... *A61B 5/7207* (2013.01); *A61B 5/7264* (2013.01); *A61B 5/746* (2013.01); *A61B 5/055* (2013.01); *A61B 6/032* (2013.01); *A61B 6/037* (2013.01); *A61B 8/13* (2013.01)

(58) Field of Classification Search
 CPC ......... A61B 5/746; A61B 5/055; A61B 6/032; A61B 6/037; A61B 8/13
 See application file for complete search history.

(56) References Cited

U.S. PATENT DOCUMENTS

| | | | |
|---|---|---|---|
| 2008/0242968 A1* | 10/2008 | Claus | G06K 9/20 600/407 |
| 2011/0110572 A1* | 5/2011 | Guehring | A61B 6/545 382/131 |
| 2015/0137988 A1* | 5/2015 | Gravenstein | A61B 5/14551 702/19 |
| 2016/0058426 A1* | 3/2016 | Hedlund | A61B 8/14 600/407 |
| 2016/0324500 A1* | 11/2016 | Fan | G01R 33/5676 |
| 2017/0351937 A1 | 12/2017 | Lu et al. | |
| 2017/0365047 A1 | 12/2017 | Beque et al. | |
| 2017/0372476 A1 | 12/2017 | Bhatia et al. | |
| 2018/0100907 A1 | 4/2018 | Soza et al. | |
| 2019/0167203 A1 | 6/2019 | Paul et al. | |
| 2019/0298210 A1* | 10/2019 | Bennet | G06K 9/00496 |
| 2019/0362835 A1* | 11/2019 | Sreenivasan | G06T 7/0012 |

OTHER PUBLICATIONS

German action dated Nov. 9, 2018 for German Application No. 10 2018 207 632.4.

\* cited by examiner

SYSTEM AND METHOD FOR DETERMINING AN IMAGING MODALITY AND THE PARAMETERS THEREFOR

CROSS REFERENCE TO RELATED APPLICATIONS

This patent application claims priority to German Patent Application No. 102018207632.4, filed May 16, 2018, which is incorporated herein by reference in its entirety.

BACKGROUND

Field

The present disclosure relates to the determination of an imaging modality and the determination of the parameters of this determined imaging modality.

Related Art

Medical imaging modalities such as e.g. magnetic resonance tomography, computed tomography, positron emission tomography, single-photon emission computed tomography or X-ray scan are susceptible in all variety of ways to patient-specific interfering influences. The greatest interfering influence in this case is that of patient movement, which causes movement artifacts in the generated image in all imaging modalities. In the case of computed tomography, such patient movements are shown as stripes and dual contours, while a patient movement in the context of MR imaging may have different effects depending on the imaging sequence and the parameters that are set. In particular, in the case of the sequence that is most frequently used in clinical practice, the turbo-spin echo sequence, patient movement will often cause phantom artifacts which restrict the diagnosis, make a diagnosis impossible, or make a new recording necessary. Furthermore, interfering influences can also be brought about by physiological causes such as heartbeat or respiration, or by a foreign body such as an implant.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
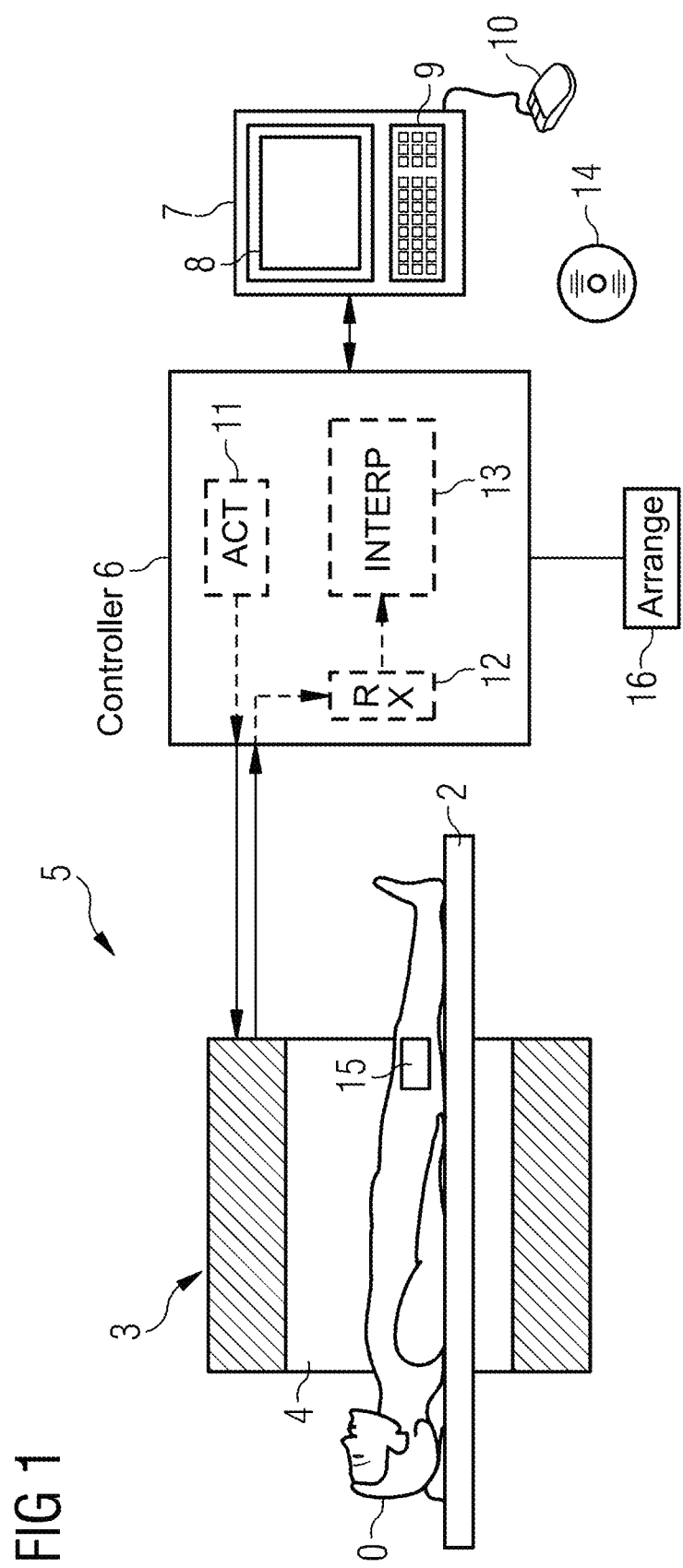
FIG. 1 is a schematic illustration of an imaging system according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to minimize, restrict, or otherwise reduce influences of patient-specific interfering influences on the images generated using a medical imaging modality.

In the present disclosure, a method is provided for determining a medical imaging modality and the parameters to be deployed in this case for the determined imaging modality. An image of an examination object, such as a human patient, is produced using this determined imaging modality and the determined parameters.

In an exemplary embodiment, the method includes automatically classifying information captured from preliminary examinations of the examination object. This classification provides classification results, which may include interfering influences that are to be expected when producing the image of the examination object. The classification examines the quasi information available from the preliminary examinations, in particular with regard to interfering influences, to classify this information and therefore the interfering influences and the examination object. In an exemplary embodiment, the method further includes analyzing the classification results to evaluate the classification results. In an exemplary embodiment, the classification results are interpreted to determine an (ideally optimal) imaging modality and to perform/apply the associated parameters based on the interpretation. In an exemplary embodiment, a decision about the imaging strategy for the pending examination is derived from the analysis of the classification results. In an exemplary embodiment, the method further includes determining the imaging modality and the parameters to be deployed for the determined imaging modality, as a function of (e.g. based on) the evaluated results. In an exemplary embodiment, the imaging modality and the parameters to be deployed are determined such that, in the images of the examination object that are generated using the determined imaging modality and the determined parameters, the influence of the previously classified interfering influences are reduced or minimized. In this example, the imaging modality and the deployed parameters are determined such that the previously identified and classified interfering influences have minimal influence and result in the fewest possible artifacts in the current images of the examination object. Here, the images are produced using the determined imaging modality and the determine parameters.

In exemplary embodiments of the present disclosure, information is ascertained or otherwise determined/obtained about interfering influences, as part of the production of an image of an examination object using an imaging modality, based on the information from preliminary examinations of the examination object. By interpreting and classifying this information, including the interfering influences included therein, an imaging modality and corresponding parameters are advantageously determined, which may be customized for the individual examination object. These determinations advantageously reduce and/or minimize the influences of the classified interfering influences in the images of the examination object that are to be produced.

The determining or deciding which imaging modality and which parameters are to be deployed for the purpose of producing an image of the examination object can output the decision in the form of a recommendation (e.g. in text format) to the operating personnel, for example. As explained in greater detail below, automatic presetting of the examination parameters is performed in an exemplary embodiment.

In an exemplary embodiment, the method is applied for temporally separated measurements. In an exemplary embodiment, the imaging modality and the parameters to be deployed are automatically determined or selected based on the interfering influences that occurred in preliminary examinations to remove other reduce/minimize these interfering influences.

In an exemplary embodiment, the information gained from the preliminary examinations of the examination object includes interfering influences within images of the examination object which were produced during these preliminary examinations or previously using known imaging modalities and known parameters. In an exemplary embodiment, the images are automatically interpreted with regard to the interfering influences during the classification to obtain the results of the classification. In an exemplary embodiment, the old images of the examination object are analyzed with respect to the interfering influences such that the results of this classification correspond to a classification (e.g. quasi classification) of the interfering influences and therefore a classification of the examination object.

In an exemplary embodiment, the classification of the interfering influences includes identifying and classifying movement artifacts as the interfering influences in the earlier images of the examination object, Identifying and classifying implants in the examination object as the interfering influences in the earlier images of the examination object, and/or capturing information from an operator to advantageously improve the classification of the interfering influences.

In an exemplary embodiment, each of these images are classified using a convolutional neural network (CNN) to identify and classify movement artifacts as the interfering influences in the earlier images of the examination object. In an exemplary embodiment, the CNN is trained in advance to identify movement artifacts in images. After the training, the CNN identifies movement artifacts in an image with almost the same degree of precision as a doctor.

In an exemplary embodiment, existing image flaws in the images are classified as the interfering influences using a convolutional neural network (CNN) to identifying and classify implants in the examination object as the interfering influences in the earlier images of the examination object. In an exemplary embodiment, the CNN is also trained in advance to ascertain the type and position of an implant in the examination object based on the image flaws or interfering influences that are present in the respective image.

In an exemplary embodiment, information from an operator is obtained/captured or otherwise determined/provided to improve the classification of the interfering influences. In this example, information, e.g. from the operating personnel or the referring doctor, may contribute to the classification of the interfering influences. This information can be captured based on a selection (e.g. using a selection box) at the end of the respective examination.

According to one or more exemplary embodiments, classification of the interfering influences is advantageously improved, and thereby the determination of the imaging modality and the deployed parameters are also advantageously improved. This advantageously further minimizes the effects of the classified interfering influences in the image of the examination object produced thereby.

In an exemplary embodiment, an image of the examination object is produced using the determined imaging modality and the determined parameters of the determined imaging modality. The produced image may then be added to other images based on the classified interfering influences.

In an exemplary embodiment, the classification information and/or image information are updated, such as at the end of the current examination. Advantageously, the determination of the imaging modality and of the parameters to be deployed is further improved for a subsequent examination of the examination object.

In an exemplary embodiment, at the end of the current examination, an item of information (e.g. feedback) from the operator can be requested and then used to evaluate the effectiveness and quality of the determined imaging modality and the determined parameters relating to an examination of the individual examination object. This information can then be deployed in subsequent repetitions of the method of the present disclosure to further improve the classification, analysis, and/or determination operations.

In an exemplary embodiment, information from the preliminary examinations includes: (a) movement trajectory information describing a movement of the examination object during one of the preliminary examinations. The probability of movement artifacts can be estimated on the basis of this movement trajectory; (b) a respiration curve of the examination object during one of the preliminary examinations. Irregularities during the respiration can be captured based on the respiration curve. A time duration for which the examination object is able to hold their breath can also be ascertained on the basis of the respiration curve; (c) an ECG curve of an ECG of the examination object during one of the preliminary examinations; (d) a pulse rate of the examination object during one of the preliminary examinations; (e) a number of attempts of the examination object to make contact with the operating personnel during one of the preliminary examinations. The attempt to make contact with the operating personnel often results in an interruption of the measurement, whereby the measurement is prolonged and therefore the effectiveness of the measurement is negatively affected. The attempt to make contact occurs more frequently, for example, in the case of patients who suffer from claustrophobia; (f) a number of communication connections established between the examination object and the operating personnel during one of the preliminary examinations. The attempt to make contact usually results in a communication connection being established between the examination object and the operating personnel, which then often results in the previously described interruption of the measurement; and/or (g) a number of repetitions of examinations of the examination object during one of the preliminary examinations, or of futile examinations of the examination object during one of the preliminary examinations. The information is not limited and may include other information as would be understood by one of ordinary skill in the art.

Based on the information described above, it is possible to classify the examination object very precisely, such that as far as possible an optimal imaging modality and the corresponding parameters can be determined as a function of this information, in order to produce an image of the examination object as effectively as possible.

In an exemplary embodiment, the classification is performed by one or more classifiers. If a plurality of classifiers are used, each of these classifiers can be used to classify a specific type of interfering influences, e.g. interfering influences that are generated by movement or interfering influences that are generated by an implant. In an exemplary embodiment, the classifier(s) includes processor circuitry that is configured to perform one or more classifications. In an exemplary embodiment, the controller 6 (FIG. 1) includes one or more classifiers.

In an exemplary embodiment, the classification is executed either directly at the respective imaging device (i.e. device that performs the imaging modality) of the preliminary examination as part of the preliminary examination (i.e. the examination that was carried out before the current examination) or retrospectively. In this aspect, the classification can be executed either by the imaging device itself or on a separate computer or server. In the latter case, for example, an analysis server or even a cloud-based solution which is linked to the PACS (Picture Archiving and Communication System) of a hospital may be used.

In an exemplary embodiment, the results of the classification includes one or more or more of the following: (a) One or more quality numerical values which derive in each case, as a function of the information, a numerical value relating to the quality of earlier images of the examination object that were produced using a determined imaging modality. Using these quality numerical values, it is possible to evaluate e.g. the quality of a fat saturation in the earlier images of the examination object; (b) One or more movement numerical values which indicate in each case a numerical value for the degree to which a movement of the examination object caused the interfering influences. The respective movement numerical value therefore corresponds to an indication (e.g. quasi indication) of the extent (e.g. percentage) to which the movement of the examination object caused the interfering influences that were captured. In this way, the respective movement numerical value reflects the degree to which the movement of the examination object negatively affects the ease of diagnosis on the basis of the images that are produced, depending on the respective query that is to be answered by the images. In this case, a continuous patient movement must usually be considered more critical than a few sudden movements within the measurement. A first movement numerical value may describe, for example, the average displacement of the examination object, while a second movement numerical value describes the regularity of the movements of the examination object; (c) An implant type of an implant in the examination object. Based on the interfering influences, and therefore as a result of the classification of these interfering influences, it is also possible to determine the type of an implant in the examination object relatively accurately. The imaging modality can then be determined as a function of the implant type; (d) A geometrical extent of an implant in the examination object. Based on the interfering influences, and therefore as a result of the classification and interpretation of these interfering influences, it is also possible to determine the dimensions of the implant in the examination object; and/or (e) A recommendation in respect of a support aid, which can support the examination object during the production of images of the examination object. Such a recommendation is prudent, for example, if a tremor occurs after some minutes or occurs at all in the examination object.

In an exemplary embodiment, given that the classification results include the quality numerical value, the movement numerical value, the implant type, the geometrical extent of the implant and/or the recommendation in respect of the support aid, the classification results advantageously contain supplementary information for the determination of the imaging modality and the parameters to be deployed for determining the modality.

Examples of information or interfering influences are described below that result from the determined classification and/or, on the basis of the analysis of the classification results, the determined imaging modality. In an exemplary embodiment, the specified sequences or supplementary information for executing the respective imaging modality correspond to the parameters to be determined in accordance with the disclosure, which parameters are to be deployed for the determined imaging modality.

If very distinct movement artifacts can be identified within the earlier images, this may result in a very poor classification in respect of movement (e.g. movement note 6), and therefore MR imaging with only very short sequences (e.g. a HASTE sequence (Half Fourier Acquisition Single shot Turbo spin Echo) instead of a TSE sequence (Turbo Spin Echo)) is determined as an imaging modality for the purpose of examining the examination object.

If moderately distinct movement artifacts can be identified within the earlier images, this may result in a moderate classification in respect of movement (e.g. movement note 3), and therefore MR imaging with movement-resistant sequences (e.g. a TSE-BLADE sequence instead of the TSE sequence) is determined as an imaging modality for the purpose of examining the examination object. (BLADE signifies a specific procedure for sampling K-space, in the form of parallel periodically rotating overlapping K-space lines, which allows improved reconstruction of the MR images.)

If slight movement artifacts can be identified within the earlier images, this may result in a good classification in respect of movement (movement note 2), and therefore MR imaging with sequences in which averaging takes place more than once (e.g. TSE sequences in which averaging takes place twice) is determined as an imaging modality for the purpose of examining the examination object.

If very distinct metal artifacts can be identified within the earlier images, this may result in a very poor classification in respect of implants (e.g. implant note 6). In this case, MR imaging will not result in MR images of sufficient quality and therefore e.g. computed tomography is determined as an imaging modality.

If only faint metal artifacts can be identified within the earlier images, this may result in a satisfactory classification in respect of implants (implant note 3), and therefore MR imaging with e.g. the SEMAC method (Slice Encoding for Metal Artifact Correction) is again determined as an imaging modality for the purpose of examining the examination object.

If no metal artifacts can be identified within the earlier images, this may result in a very good classification in respect of implants (implant note 1), and therefore MR imaging with e.g. a standard TSE sequence is determined as an imaging modality for the purpose of examining the examination object.

If good fat saturation can be identified within the earlier images, MR imaging with time-optimized sequences using SPAIR saturation pulses (Spectrally Adiabatic Inversion Recovery) can be determined as an imaging modality. In this case, the quality of the fat saturation in the respective examination object can be estimated on the basis of identifiable fat saturation results in the earlier images of the examination object.

However, if poor fat saturation can be identified within the earlier images, MR imaging with sequences based on Dixon methods can be determined as an imaging modality.

By taking poor fat saturation into consideration in earlier images when determining the imaging modality and the parameters to be deployed in this case, it is advantageously possible to avoid the problem that specific body characteristics produce a poor shim result, wherein chemical shift artifacts or destructive image interference occur due to inadequate fat suppression in particular.

The information gained from the preliminary examinations can also be used in the context of different modalities. If a metal prosthesis of a specific size is identified in an earlier CT image, for example, it is possible as a function thereof inventively to determine MR imaging with an MR measuring sequence that is insensitive to metal artifacts, or an ultrasound examination with an ultrasound mode or ultrasound probe which minimizes the risk of the metal implant working loose or the occurrence of artifacts, as an imaging modality.

A pacemaker (e.g. a cardiac pacemaker) can also be identified in an earlier CT image or ultrasound image. As a function of this information, it is then possible either to prohibit MR imaging from being determined as an imaging modality or to determine MR imaging with only low MR field strengths or an imaging mode with reduced HF power and gradient slew rate as an imaging modality.

The classification results can be associated and stored with meta-information relating to the examination object in storage means (e.g. a database). The classification results can also be directly associated with the medical image data of the examination object as DICOM attribute(s).

In an exemplary embodiment, the operations for the classification of the interfering influences, the analysis of the classification results, and/or the determination of the imaging modality and/or the parameters may be implemented: based on one or more rules; as a machine learning algorithm, which can include the interpretation of big data; and/or in the form of a convolutional neural network.

In an exemplary embodiment, the analysis of the classification results advantageously include a weighting of the results of the classification. In this case, the following possibilities are available according to the disclosure and can be combined correspondingly: Chronologically more recent classification results are weighted more highly than chronologically older results. In other words, classification results obtained from the interpretation of more recent images are given a higher weighting than results obtained from the interpretation of older images.

The more recent the images of the examination object, where said images were interpreted to produce the results, the higher the weighting of the results; If, according to an inventive embodiment variant, the imaging modality is stipulated and therefore corresponds to the imaging modality that is to be determined, classification results obtained on the basis of images of the examination object, where said images were recorded using the stipulated imaging modality, are weighted more highly than results obtained on the basis of images that were produced using a different imaging modality; Classification results that were produced on the basis of earlier images of the examination object, where said images were recorded for a body region (of the examination object) which must also be recorded by the image that is to be produced, are weighted more highly than results produced on the basis of earlier images which concern other body regions of the examination object; and/or Classification results that were produced on the basis of earlier images of the examination object, where said images were produced using an imaging modality that is more susceptible to a specific interfering influence than other imaging modalities, are weighted more highly. For example, if dual contours suggest a movement of the examination object in earlier CT images of the examination object, but no movement artifacts are revealed in earlier MR images and an MR recording is now to take place, the results obtained on the basis of the earlier MR images are weighted more highly. It is assumed that the reliability of classification results obtained from the same imaging modality is higher than when expected results in the case of another imaging modality have to be inferred from classification results obtained from a different imaging modality.

In an exemplary embodiment, the classification results are combined with different weightings in the analyzation of the results, and thus transferred to the operation for determining the imaging modality and the parameters to be deployed. As described above, for example, the most recent available classification can therefore be weighted more highly than older classifications. If the current available classification indicates the presence of an implant in the examination object while older classifications still do not, for example, there is a high probability that the implant was only recently installed and must with immediate effect be taken into consideration when determining the imaging modality and the parameters to be deployed.

In an exemplary embodiment, one or more analyzers which, depending on an input of the patient-specific classification results, are configured to perform the analysis of these results. The analyzer(s) may be arranged directly at the imaging device of the current examination or may equally be located on a separate system, e.g. the radiology information system (RIS) of the hospital. In an exemplary embodiment, the analyzer includes process circuitry that is configured to perform analyze the results.

In an exemplary embodiment, the determination method also includes automatically setting the parameters of the determined imaging modality to the parameters that are determined beforehand for the determined imaging modality. Therefore the method according to an exemplary aspect includes not only the determination of the imaging modality and the parameters to be deployed in this case, but also includes an automatic setting of these parameters, such that an image of the examination object can be produced quasi automatically using the determined imaging modality and the determined parameters.

In an exemplary embodiment, as part of the determination of a magnetic resonance facility as the determined imaging modality, the determination of the parameters also includes determining or deciding which imaging technique or sequence will be deployed for the purpose of capturing the image. For example, a sequence based on BLADE can be deployed to reduce movement influences and a sequence based on SEMAC to reduce metal artifacts. Using other sequence types, it is possible to limit hardware restrictions for safe recording of an examination object which has an implant or to shorten the breath-holding time.

A BLADE-based sequence is intrinsically resistant to movements of the examination object during the recording, since K-space is sampled in the manner of a propeller and therefore each sampled K-space segment contains K-space center, whereby K-space centers can be registered in relation to each other. In other words, and in particular in the case of examination objects for which the movement numerical value or movement note lies below a specified threshold, a TSE sequence with a BLADE option is determined for the purpose of capturing the required image data. In particular, in the case of examination objects for which the movement numerical value or movement note lies below the specified threshold, either more averaging is employed in order to even out any movement of the examination object that occurs, or the measuring time is kept as short as possible, e.g. by capturing fewer K-space points, in order thereby to reduce the probability of movements occurring during the measurement.

In an exemplary embodiment, the imaging modality to be determined is stipulated. In this embodiment, a warning is generated/output before an image of the examination object is produced using the stipulated imaging modality if it is automatically identified that the classification results prohibit production of an image of the examination object using the stipulated imaging modality.

In an exemplary embodiment, the examination of the examination object (i.e. the production of an image of the examination object) may be refused if the analysis of the results of the classification produces a contraindication, as the examination would result in risk to the patient, for example.

In an exemplary embodiment, the imaging modality includes one of the following modalities: magnetic resonance tomography, computed tomography, positron emission tomography, single-photon emission computed tomography, ultrasound, or X-ray. The imaging modality is not limited and may include an imaging modality as would be understood by one of ordinary skill in the art.

The method as described in the present disclosure have the following advantages: A patient-specific examination or production of an image of the examination object is achieved; The present disclosure ensures greater safety if implants are present (including prosthetic teeth).

Possible erroneous information from an explanatory talk is revealed and/or avoided; The image quality of an image produced according to the disclosure is higher at least on average than it is for imaging modalities according to the prior art, whereby the ease of diagnosis is also positively affected; In comparison with the prior art, time is saved during the production of an image of the examination object. Unnecessary patient handling and repetitions of the image production are avoided; The present disclosure is not restricted to one imaging modality, but can also comprise the selection or determination of the imaging modality to be deployed, or used for any imaging modalities; and The present disclosure supports the operating personnel in the production of images of the examination object, and results in greater patient satisfaction in comparison with the prior art.

In an exemplary embodiment, an arrangement (i.e. determination system) configured to determine a medical imaging modality and the parameters to be deployed for the determined imaging modality to produce an image of an examination object using the determined imaging modality and the parameters determined for the determined modality. In an exemplary embodiment, the system includes a controller configured to classify information (e.g. the information may be known from preliminary examinations of the examination object and stored in a storage device (e.g. memory) included in the system and/or communicatively coupled to the system. In an exemplary embodiment, the controller is configured to classify the information with regard to interfering influences to be expected when producing the image to obtain classification results. In an exemplary embodiment, the controller is further configured to analyze the results to evaluate the results based on the analysis, and to determine the imaging modality and the parameters as a function of the evaluated results, such that the classified interfering influences are reduced and/or minimized in images of the examination object that are produced using the determined imaging modality and the determined parameters.

The advantages of the system according to the exemplary embodiments described herein correspond essentially to the advantages of the method according to one or more embodiments described in detail above.

In an exemplary embodiment, an imaging system includes a medical imaging modality, e.g. a magnetic resonance facility, and the determination system of one or more exemplary embodiments. In an exemplary embodiment, the imaging system is configured to set parameters of the imaging modality of the imaging system according to the parameters that are determined beforehand by the determination system (i.e. arrangement), and to produce an image of the examination object using the imaging modality of the imaging system and the parameters that have been set.

In an exemplary embodiment, a computer program product (e.g. software), which can be loaded into a memory of a programmable controller or a computer of the imaging system. The computer program product may be stored on a memory storage device (e.g. a non-transitory computer readable medium). In an exemplary embodiment, execution of the computer program product causes the controller to perform one or more operations and/or functions according to one or more aspects of the present disclosure. In an exemplary embodiment, computer program product may require program resources (e.g. libraries and help functions) to realize the corresponding embodiments of the method. In an exemplary embodiment, the computer program product includes software that causes a controller (e.g. processor) to execute a method according to one or more exemplary embodiments. In an exemplary embodiment, the software can be source code (e.g. C++), which must then be compiled and linked or which merely has to be interpreted, or executable software code, which merely has to be loaded into the corresponding computer or controller for execution.

The present disclosure is also directed to an electronically readable data medium, e.g. a DVD, a magnetic tape, a hard disk a USB stick, and/or other memory, on which is stored electronically readable control information, in particular software (see above). In an exemplary embodiment, when this control information is read from the data medium and stored in a controller or computer of an imaging system according to the disclosure, the method according to an exemplary embodiment is executed.

FIG. 1 shows an imaging system according to an exemplary embodiment of the disclosure. FIG. 1 schematically shows an imaging system that includes a magnetic resonance facility 5 (as medical imaging modality) and an arrangement (determination system) 16 configured to determine a medical imaging modality and the parameters to be deployed for the determined imaging modality. In an exemplary embodiment, the magnetic resonance facility 5 includes a scanner 3 configured to generate the magnetic field required for the MR examination in a measurement chamber 4, a table or couch 2, a controller 6 configured to control the scanner 3 and capture MR data from the scanner 3, and a terminal 7 connected to the controller 6. In an exemplary embodiment, the controller 6 includes processor circuitry that is configured to perform one or more operations and/or functions of the controller 6, including, for example, controlling the scanner 3 and capturing MR data from the scanner 3.

In an exemplary embodiment, the controller 6 includes an activator 11, a receiver 12, and an interpreter 13. In an exemplary embodiment, during the production of an image data record, MR data is captured by the receiver 12 using the scanner 3, where the scanner 3 and the table 2 can be activated by the activator 11 in such a way that MR data is captured in a measurement volume 15 that is situated within the body of a patient O lying on the table 2.

In an exemplary embodiment, the interpreter 13 is configured to then prepare (e.g. converts) the MR data in such a way that it can be graphically represented on a display screen 8 of the terminal 7. In addition to graphical representation of the MR data, the terminal 7 can include a keyboard 9 and a mouse 10 (or other input devices) in addition to the display screen 8. These input devices (e.g. keyboard 9 and/or mouse 10) can be used by a user to capture/enter information for the purpose of classifying the examination object and/or the interfering influences. The terminal 7 can also be used to load the software for the controller 6 into the controller 6. This software for the controller 6 can also contain the method according to one or more of the exemplary embodiments described in the present disclosure. In an exemplary embodiment, a method according to the disclosure is included in software which runs on the terminal 7. Irrespective which software contains the exemplary method, the software can be stored on a DVD 14 (or other storage memory), such that the software can then be read from the DVD 14 by the terminal 7 and copied into the controller 6 and/or a computer of the terminal 7 itself.

Since the imaging system shown in FIG. 1 only has one imaging modality, the imaging system is also able to determine an imaging modality other than the magnetic resonance facility 5 that is present in the system using the arrangement/determination system 16. In this example, the imaging system is not able to produce any images using this other imaging modality. In an exemplary embodiment, the imaging system includes a plurality of imaging modalities (e.g. additionally a computed scanner and an X-ray modality) to determine, from these imaging modalities that are present in the system, which modality is most suitable for the examination and then to produce an image of the examination object using this determined imaging modality and the parameters determined for the modality.

Figure 2:
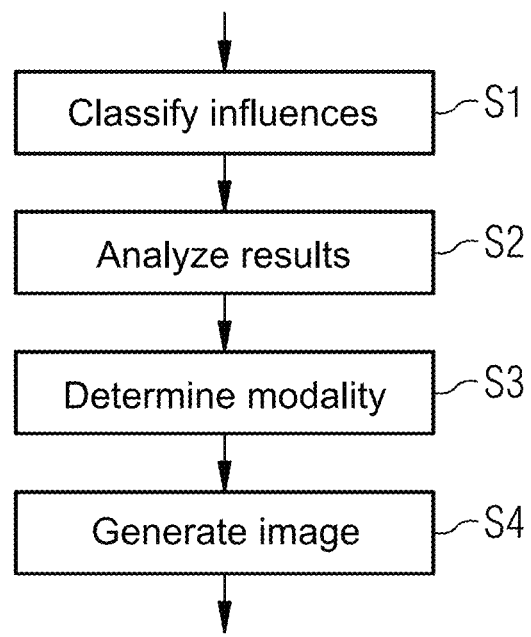
FIG. 2 illustrates a flowchart of a method for determining a medical imaging modality and parameter to be deployed for the determined imaging modality according to an exemplary embodiment of the present disclosure.

FIG. 2 shows a flowchart of a method according to an exemplary embodiment of the disclosure for determining a medical imaging modality and the parameters to be deployed for the determined imaging modality.

In an exemplary embodiment, the method includes the following steps S1-S4. In the first step S1, information (e.g. earlier images, of the examination object or patient) is interpreted to classify interfering influences, e.g. in the earlier images. The results of this classification from the first step S1 are analyzed in the second step S2 to evaluate the classification results. Based on the results of the analysis in step S2, the imaging modality that is to be used to produce a current image of the patient is determined in step S3. In an exemplary embodiment, step S3 additionally includes the determination of the parameters of the determined imaging modality in such a way that, in the images of the patient that are produced using the thus determined imaging modality and the determined parameters, the classified interfering influences are reduced and/or minimized. In step S4, an image of the patient is produced or otherwise generated using the determined imaging modality and the determined parameters.

CONCLUSION

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," "aspect," "aspects," etc., indicate that the embodiment or aspect described may include a particular feature, structure, or characteristic, but every embodiment or aspect may not necessarily include the particular feature, structure, or characteristic. Moreover, such phrases are not necessarily referring to the same embodiment or aspect. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM);

magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, other structural electronic hardware, or a combination thereof. A processor includes a microprocessor, a digital signal processor (DSP), central processing unit (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for determining a medical imaging modality, from a plurality of imaging modalities, and one or more parameters thereof, to be used to produce an image of an examination object, the method comprising:
   providing a trained convoluted neural network (CNN) with information obtained from one or more preliminary examinations of the examination object and generating classification results via the trained CNN according to a degree that one or more interfering influences have an influence on the information, wherein the information comprises (i) a movement trajectory of a movement of the examination object during a preliminary examination, and (ii)
   a number of attempts of the examination object to make contact with operating personnel during a preliminary examination,
   analyzing the classification results via the trained CNN to evaluate the classification results and determining a medical imaging modality and one or more parameters thereof from among said plurality of imaging modalities that minimize the influence of the one or more interfering influences in one or more images of the examination object to be generated using the determined medical imaging modality and the determined one or more parameters thereof; and
   representing the determined image modality and the one or more parameters thereof in an electronic output from the trained CNN.

2. The method according to claim 1, wherein the information comprises interfering influences within images of the examination object that were previously produced using one or more imaging modalities and parameters, the images being automatically interpreted based on the interfering influences.

3. The method according to claim 2, wherein generating the classification results comprises at least one of the following operations:
   classifying movement artifacts as the interfering influences in the images, wherein each image is classified by the CNN;
   classifying one or more implants of the examination object, wherein image flaws that are present as the interfering influences in the images are classified as implants by a convolutional neural network; and
   capturing information from an operator to improve the classification.

4. The method according to claim 2, wherein:
   the electronic output comprising an image of the examination object generated based on the determined medical imaging modality and the determined one or more parameters; and
   the method further comprises adding the generated image to images from which the interfering influences are classified.

5. The method according to claim 1, wherein the electronic output comprises an image of the examination object generated based on the determined medical imaging modality and the determined one or more parameters.

6. The method according to claim 1, wherein the information further comprises
   a pulse rate of a pulse of the examination object during a preliminary examination.

7. The method according to claim 1, wherein the classification results comprise:
   at least one quality numerical value derives, based on the information, at least one numerical value corresponding to a quality of images of the examination object produced using an imaging modality;
   at least one movement numerical value indicative of a degree to which a movement of the examination object caused the interfering influences;
   an implant type of an implant in the examination object;
   a geometrical extent of an implant in the examination object; and/or
   a recommendation associated with a support aid for the examination object when producing images of the examination object using an imaging modality.

8. The method according to claim 1, wherein the analyzing the classification results comprises weighting the classification results, wherein:
   chronologically more recent results are weighted more highly;
   results obtained using an imaging modality that is stipulated as the imaging modality to be determined are weighted more highly;
   results relating to that body region of the examination object for which the image is to be produced are weighted more highly; and/or
   results obtained using an imaging modality that is more susceptible to a determined interfering influence are weighted more highly.

9. The method according to claim 1, further comprising: automatically setting parameters to be deployed to the one or more parameters that are determined for the determined imaging modality.

10. The method according to claim 1, wherein:
    the imaging modality to be determined is stipulated; and
    the method further comprises generating a warning before an image of the examination object is produced using the stipulated imaging modality if the classification results prohibit production of an image of the examination object using the stipulated imaging modality.

11. The method according to claim 1, wherein the determined imaging modality comprises magnetic resonance tomography, computed tomography, positron emission tomography, single-photon emission computed tomography, an ultrasound modality or an X-ray modality.

12. A non-transitory computer readable medium that stores a program, that when executed, causes a controller to perform the method of claim 1.

13. The method according to claim 1, wherein the information further comprises the respiration curve of respiration of the examination object during a preliminary examination.

14. The method according to claim 1, wherein the information further comprises the ECG curve of an ECG of the examination object during a preliminary examination.

15. The method according to claim 1, wherein the information further comprises (i) a number of communication connections established between the examination object and operating personnel during a preliminary examination, and/or (ii) a number of repetitions of examinations or futile examinations of the examination object during a preliminary examination.

16. The method according to claim 1, wherein the information further comprises (i) the respiration curve of respiration of the examination object during a preliminary examination and (ii) the ECG curve of an ECG of the examination object during a preliminary examination.

17. The method according to claim 1, wherein the information further comprises (i) a number of communication connections established between the examination object and operating personnel during a preliminary examination, and (ii) a number of repetitions of examinations or futile examinations of the examination object during a preliminary examination.

18. A system for determining a medical imaging modality, from a plurality of imaging modalities, and one or more parameters thereof, to be used to produce an image of an examination object, the system comprising:
   a memory that stores information obtained from one or more preliminary examinations of the examination object, wherein the information comprises (i) a movement trajectory of a movement of the examination object during a preliminary examination, and (ii)
   a number of attempts of the examination object to make contact with operating personnel during a preliminary examination
   a controller communicatively coupled to the memory, and that is configured to:
      generate, via a trained convoluted neural network (CNN), classification results according to a degree that one or more interfering influences have an influence on the information;
      analyze the classification results to evaluate the classification results and determine a medical imaging modality and one or more parameters thereof from among the plurality of imaging modalities that minimize the influence of the one or more interfering influences in one or more images of the examination object to be generated using the determined medical imaging modality and the determined one or more parameters thereof; and
      generate an electronic output representing the determined image modality and the one or more parameters thereof.

19. The system according to claim 18, wherein the controller is further configured to control an imaging system to generate an image of the examination object based on the determined medical imaging modality and the determined one or more parameters.

20. An imaging system comprising:
   a medical imaging modality; and
   the system of claim 18, wherein the imaging system is configured to:
      set one or more parameters of the medical imaging modality to the determined one or more parameters determined by the system of claim 14, and
      generate an image of the examination object using the medical imaging modality and based on the one or more parameters that have been set.

* * * * *